(12) United States Patent
Bixler et al.

(10) Patent No.: US 7,292,135 B2
(45) Date of Patent: Nov. 6, 2007

(54) PATIENT MONITOR INTEGRATION INTO NURSE CALL SYSTEM AND METHOD

(75) Inventors: Craig Bixler, Saint Charles, IL (US); Scott Hutchinson, South Elgin, IL (US); Brent Bergwall, Carpentersville, IL (US)

(73) Assignee: Edwards Systems Technology, Inc., Chesrie, CT (US)

( * ) Notice: Subject to any disclaimer, the term of this patent is extended or adjusted under 35 U.S.C. 154(b) by 247 days.

(21) Appl. No.: 11/087,816

(22) Filed: Mar. 24, 2005

(65) Prior Publication Data

US 2006/0214786 A1 Sep. 28, 2006

(51) Int. Cl.
G08B 5/22 (2006.01)

(52) U.S. Cl. .............................. 340/286.07; 340/539.1; 340/539.12; 600/300; 705/2

(58) Field of Classification Search ........... 340/539.12, 340/573.1, 286.07; 600/300; 705/2
See application file for complete search history.

(56) References Cited

U.S. PATENT DOCUMENTS

2003/0149598 A1* 8/2003 Santoso et al. ................ 705/2
2003/0227386 A1* 12/2003 Pulkkinen et al. ........ 340/573.1
2006/0049936 A1* 3/2006 Collins et al. .......... 340/539.11
2006/0089539 A1* 4/2006 Miodownik et al. ........ 600/300
2006/0149589 A1* 7/2006 Wager ........................... 705/2

\* cited by examiner

*Primary Examiner*—Jeffrey Hofsass
*Assistant Examiner*—Samuel J. Walk
(74) *Attorney, Agent, or Firm*—Baker & Hostetler LLP

(57) ABSTRACT

A system for automatically integrating various patient monitoring equipment into a nurse call system is implemented by incorporating a software system agent that translates communications in the patient monitoring equipment communication channel to a software system readable format. By translating the patient monitoring system's communications, a software system or computer can interpret the communications and act accordingly by signaling staff members, doctors, etc., in a manner that was not feasible by the hardware of the patient monitoring system. By interpreting the communications and having a nurse call system translation feature in the software system agent, nurse call systems can be "coupled" to the patient monitoring system to enable a synergy between systems that were here thereto incompatible or had limited functional capabilities. By combining non-compatible or limited feature patient monitoring systems with nurse systems, and by using a software process to interpret and control responses, enhanced functionalities and alerting capabilities are made available.

31 Claims, 2 Drawing Sheets

PATIENT MONITOR INTEGRATION INTO NURSE CALL SYSTEM AND METHOD

FIELD OF THE INVENTION

The present invention relates generally to patient monitoring systems. More particularly, the present invention relates to systems and methods for integrating various patient monitoring systems into a nurse call system and for enhancing the capabilities of nurse call systems.

BACKGROUND OF THE INVENTION

Hospitals use a variety of patient monitoring equipment to alert them of potential patient needs. Many monitoring devices act in a stand-alone fashion, providing only an audible alarm when an alert condition occurs. Some of these systems provide an auxiliary contact closure output, which when connected to a nurse call system, allows a generic monitor alarm to appear at the door light, at the nurse console and hallway displays. However, not all nurse call systems are installed with auxiliary input receptacles. Even if they are, connecting the monitoring equipment to the receptacle is a manual process that requires time, skill, and has the potential for error in either the process of connecting the equipment or in the process of uniquely labeling the alarm type within the nurse call based on the type of monitoring equipment: i.e. IV drip, ventilator, or heart monitor.

Accordingly, it is desirable to provide systems and methods which minimize the need for independently connecting various monitoring equipment to dedicated or auxiliary contacts, and which exploit current communication and alerting capabilities for enhanced functionalities.

SUMMARY OF THE INVENTION

The foregoing needs are met, to a great extent, by the present invention, wherein in one aspect apparatuses and methods are provided that in some embodiments couple communication and alerting features of patient monitoring systems with nurse call systems to enable a synergized and enhanced nurse call system. In accordance with various other aspects of the present invention, communication initiated by a patient monitoring system is translated and processed to enable communication and control of input/output devices that are not conventionally compatible with the patient monitoring system.

In accordance with one embodiment of the present invention, a patient monitoring and nurse call integration system is provided, comprising a patient monitor translator, a nurse call translator, and a processor in communication with the patient monitor translator and nurse call translator, wherein the processor executes instructions which interpret translated patient monitor communication and coordinate a communication via the nurse call translator to a nurse call system.

In accordance with another embodiment of the present invention, a method for patient monitoring and nurse call integration is provided, comprising the steps of, translating communication received from a patient monitoring system, processing the translated communication to assess at least one of an alarm and event communication, updating a status table to reflect a current state of equipment-to-staff assignment, translating the processed communication into a nurse call system format, and communicating the translated processed communication to a nurse call system.

In accordance with yet still another embodiment of the present invention, a patient monitoring and nurse call integration system is provided, comprising means for translating patient monitor communications, means for translating nurse call communications, and means for processing the translated patient monitor communications and executing instructions to coordinate communication to a nurse call system via the means for translating nurse call communications.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
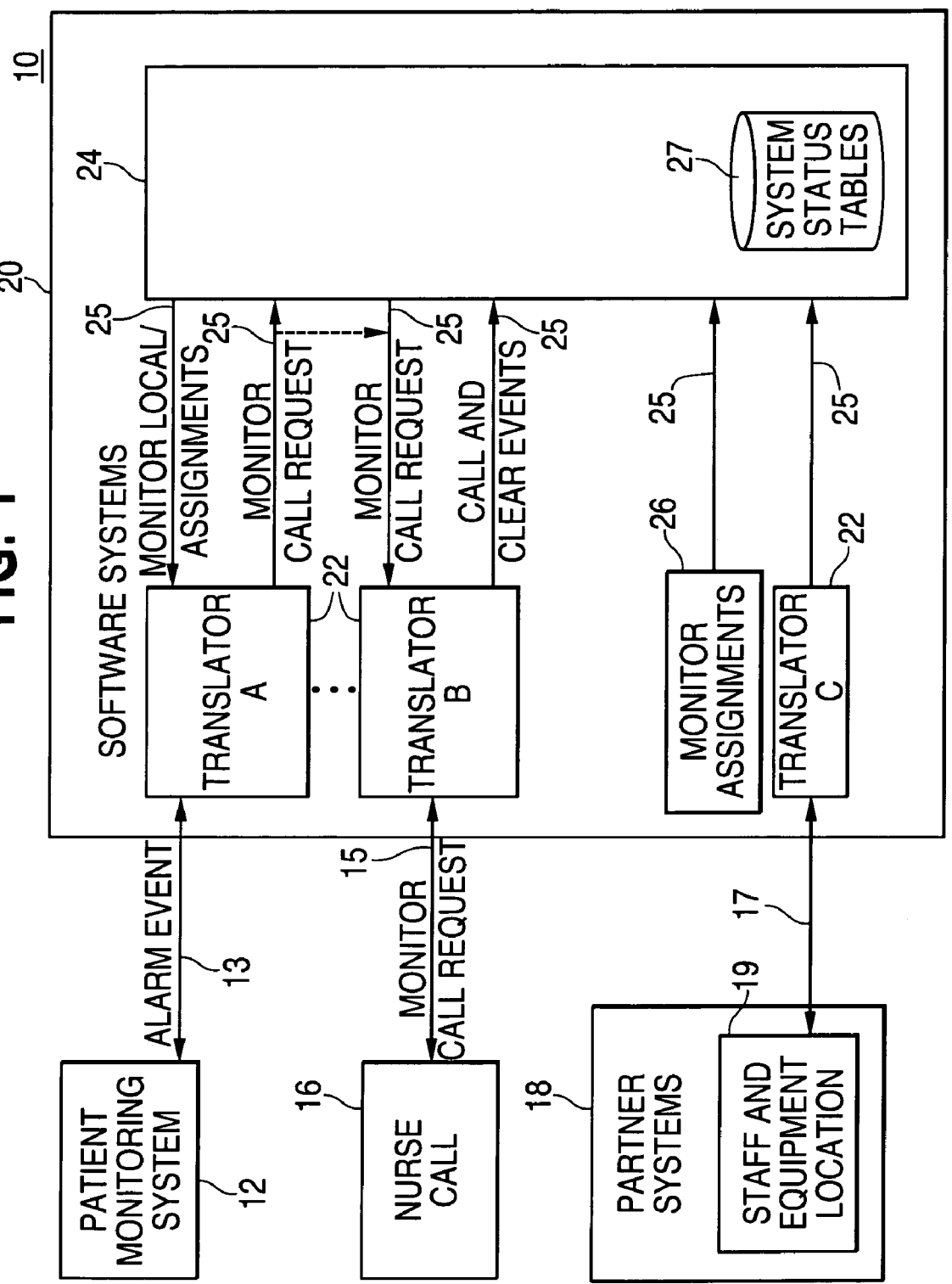
FIG. 1 is an illustration of a block diagram according to an exemplary embodiment of this invention.

The invention will now be described with reference to the drawing figures, in which like reference numerals refer to like parts throughout. An embodiment in accordance with the present invention provides systems and methods for integrating various patient monitoring equipment into a nurse call system utilizing a commonly assessable communication channel.

FIG. 1 is a block diagram of an exemplary system 10 according to this invention. The exemplary system 10 contains a patient monitoring system 12 in communication with an exemplary software-based processing system 20. Communication from the patient monitoring system 12 to the exemplary software-based processing system 20 is facilitated by an alarm/event channel 13. Also coupled to the exemplary software-based processing system 20 is a nurse call unit or system 16 via a monitor or call request channel 15. Additionally, optional partner system 18 is illustrated in FIG. 1 as being in communication with the exemplary software-based processing system 20 via communication channel 17. The optional partner system 18 may contain staff and equipment locations 19 or other desired information, for example, information concerning supplemental patient, staff, equipment, etc. status availability, condition, etc. according to design preference.

The exemplary software-based processing system 20 contains translators 22 and a monitor assignments module 26. The translators 22 and the monitor assignments module 26 exchange information with the processing module 24. The processing module 24 contains system status tables 27 relating to static and variable information germane to the patient monitoring system 12, the nurse call system 16, and the partner systems 18. Information from the status tables 27 is associated with the request from the translators 22, monitor assignment module 26, and other systems or devices as deemed necessary for facilitating the operation of the exemplary system 10. Function call pathways 25 enable communication between translators 22 and the monitor assignments module 26 with the processing module 24.

In operation, the exemplary system 10 operates in various modes depending on the degree of capability afforded by the patient monitoring system 12, nurse call system 16, and partner systems 18. For example, in one exemplary mode of operation, the exemplary system 10 may have a patient monitoring system 12, such as, for example, an EKG connected to the channel 13 to the exemplary software-based system 20. Upon the connection of the EKG monitor into the channel 13, an "updating" of the exemplary software-based system's 20 assignments and responses, etc. can be initiated via the translator 22 and via the function call pathway 25. Translator 22 may operate as a simple translator/emulator to enable conversion from different protocols or formats of the exemplary software-based system 20 to exterior systems, or as an intelligent translator having capabilities to be configured for various responses or actions.

For example, in an intelligent translator configuration, when the EKG monitor is coupled to the channel 13, the translator 22 may initiate a polling request of the processing module 24 to determine the type of monitoring device being connected to the exemplary software-based system 20, the room that the EKG monitor is located in, the patient that the EKG monitor is assigned to, the bed that the patient is residing in, contact information for alarm or event responses, or other desired information according to design preference. Accordingly, the intelligent translator 22, having been so preconfigured, may subsequently bypass the processing module 24 (illustrated in FIG. 1 as a dashed line) and immediately proceed to the call request function during an alarm event. By use of a preconfigured translator, latencies or processing time competition from other alarm events can be reduced.

Assignment monitoring information such as who is to be assigned to monitor the patient, equipment associated with the patient, and other information that may be assigned to the chain of assignable events for a designated patient monitoring system 12 can be facilitated by use of the monitor assignments module 26. The monitor assignments module 26 also may act as a verification and/or location of patient monitoring equipment 12 mechanism. Further, the monitor assignment module 26 may operate as an external data input mechanism into the processing module 24 and/or status tables 27.

In addition to the monitor assignment module's 26 ability to update the processing module 24 and database 27, partner systems 18 having staff and equipment location information 19 can similarly be used for updating and correlating information regarding the partner system 18 attributes into the system status table 27. Accordingly, for a given patient monitoring system 12, such as, for example, an EKG monitor, a database of status table 27 can have information regarding the type of EKG, location of the EKG, specific instructions regarding the use of the EKG and/or the patient and/or other treatment related information. Therefore, in addition to the basic patient monitoring system 12 and nurse call system 16 operations, the partner systems 18 can provide additional information for correlating and/or responding to an alarm or an event.

The exemplary software system 20 may be implemented in computer such as personal computer, server, networked controller, micro controllers, etc. Accordingly, the systems and methods described here may be readily implemented in software using object-oriented software development environments that can provide portable source code that can be used on a variety of computer or work station hardware platforms. Whether software or hardware is used to implement the system is dependent on the speed and efficiency requirements of the system, the particular function, and the particular software or hardware systems and microprocessor or microcomputer systems being utilized.

Accordingly, the translators 22 and the processing module 24, though implementable as a software system may be implemented either as a hardware component or software component, or a hybrid of the two. If a software implementation is utilized, any form of software containing executable or interpretable instructions may be used to accomplish the described functions. Accordingly, the programming may be an embedded code, for example, Assembler, or interpreted code, for example, Basic, or executable code, for example C, the implementation of which is based on the choice of hardware and design goals. Of course, other programming languages may be used without departing from the spirit and scope of this invention.

An advantage of the exemplary system 10 illustrated in FIG. 1, is that upon coupling or connecting of a patient monitoring system 12 into the channel 13, auxiliary information and capabilities, hereto before only available as a dedicated hardware feature, can be automatically incorporated without requiring human intervention. Thus, the use of such a system enables patient monitoring systems 12 that have a common or known output alarm or event interface such as a telelocator alarm protocol (TAP) can be "intercepted" by the exemplary software-based system 20 to enable automatic and less error prone operation of nurse call configuration and alarm events.

It should be appreciated that various modifications to the exemplary embodiment shown in FIG. 1 may be made without departing from the spirit and scope of this invention. For example, while FIG. 1 illustrates single data channels or communication channels between various components therein, multiple channels either having serial, parallel, hybrid, or other communication paradigms therein may be used, according to design preference. Additionally, while the exemplary software-based system's components are described in the context of software process or modules, some of these software modules may be replaced with hardware emulators to form a hardware/software implementation. Additionally, while system status tables 27 can originate from a database, non-database approaches may be utilized, such as, for example, spreadsheets or table lookups or chained parameter contexing. Thus, non-conventional database systems may be used such as peer-to-peer (P2P), master-slave, distributed information storing and gathering techniques may be used without departing from the spirit of the scope of this invention.

It should also be appreciated that while FIG. 1 illustrates singular elements within the exemplary system 10, with the exception of the translators, multiple elements may be used in parallel or series, such as, for example, master-slave configurations. In a preferred embodiment of the exemplary system 20, the channel 13 is a TAP channel. However non-TAP channels or means of connection/communication which may be of a proprietary protocol or of an industry standard protocol can be used. In the context of such a channel 13, the translators 22 operate to convert the information/data transmitted or received within the channel 13 to a format or type interpretable for use by the exemplary software-based system 20. For example, binary or hexadecimal coding which may be typically used when interfacing an external hardware device such as the patient monitoring system 12, or the nurse call system 16 or conversion to the database/table format for use by the processing module 24, can be effectuated by the translators 22. It should be appreciated that while FIG. 1 illustrates multiple translators operating independently and discreetly with respect to the external component, the translators 22 may be a single multitasking or multifunctional module. Accordingly, rather than using separate modules or subroutine calls, the translators may be implemented as a single multi-capable process utilizing fork or child processes to enable an asynchronous or multi-thread operations.

For example, in a preferred embodiment, a TAP output alarm which is triggered by a patient monitoring system 12, for contacting a pager carried by an on-duty nurse, is intercepted by the software translator 22 and re-routed to the nurse call system 16. The translator 22 matches the monitoring equipment ID with either the room location of the equipment from an automatic location system, or with a manually generated assignment of the equipment to a room/patient. This combination is interpreted as a patient monitor call request to a nurse call translator 22, which feeds it into the nurse call system 16.

Once in the nurse call system 16, it can be converted to a custom priority patient call. Call active feedback, both visible (LED's and/or display text) and audible (burst or repeating tone) within the room can make it clear that a monitoring device 12 has triggered an alarm. The indicating station can be a dedicated device, or dedicated signal on the existing patient station. As with any patient alarm, the monitor alarm can be given appropriate call level indications at door lights, intersection lights, and staff room, hallway and nurse station call displays.

In the above preferred embodiment example, since patient monitor equipment typically do not provide an alarm clear signal via the TAP output, the alarm remains latched into the system until manually cleared. For such a system, clearing the alarm would be initiated by a dedicated cancel switch or shared sequence on the device that is indicating the alarm. Of course, in various exemplary embodiments as shown in FIG. 1, the clearing sequence may be designated to be operated automatically from the nurse call system 16 or through feedback from an external device to the patient monitor system 12 using an auxiliary link in the channel 13, or via separate communication.

Figure 2:
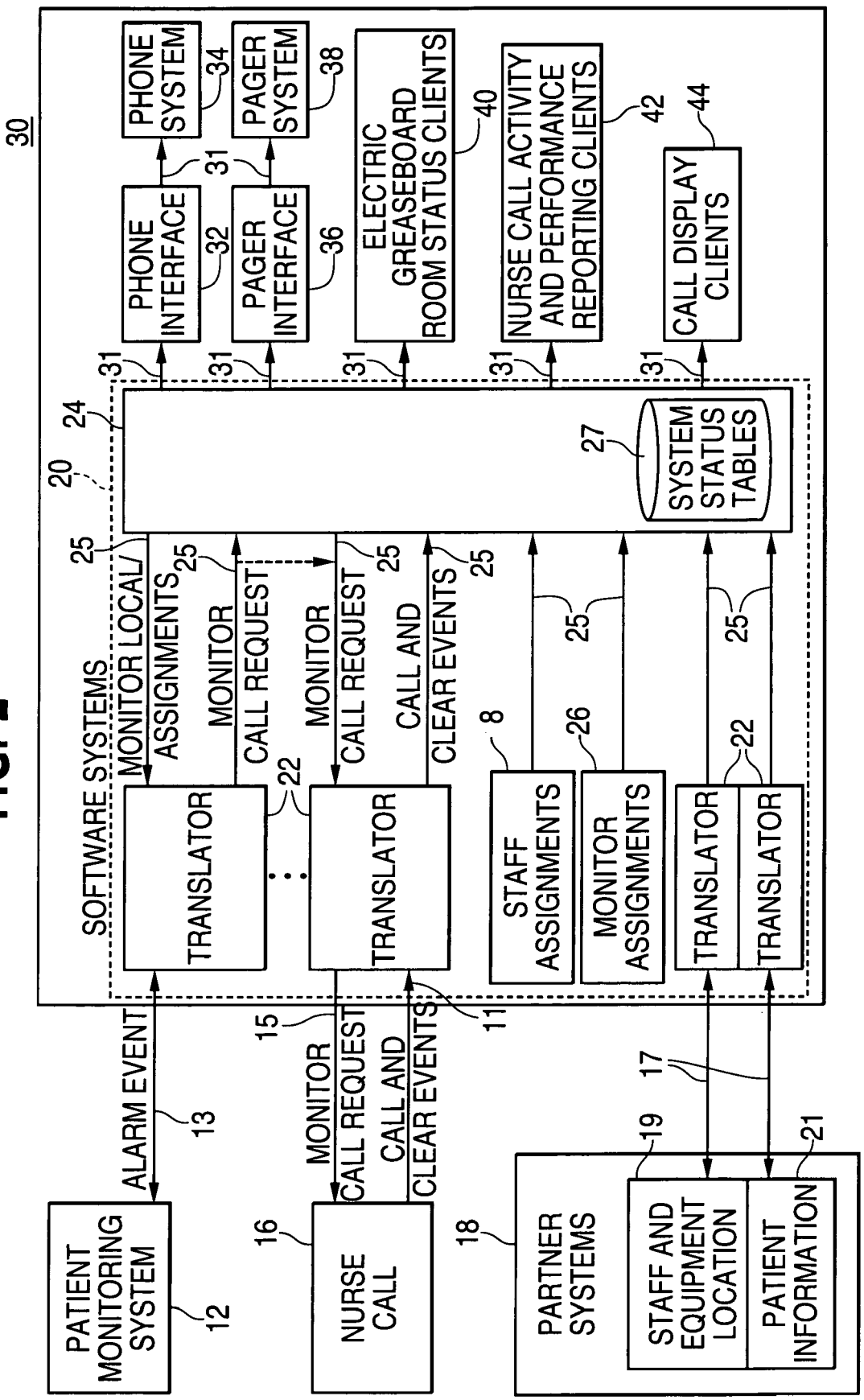
FIG. 2 is an illustration of a block diagram of another exemplary embodiment of this invention.

FIG. 2 is a block diagram of an exemplary system 30 which is an enhanced version of the exemplary system 20, described in FIG. 1. For example, in addition to having monitor assignments module 26, staff assignments module 8 is provided for incorporating information to and from the processing module 26 and the system status system tables 28.

Staff assignments module 8 enable specific assignment of staff members to designated monitoring systems, alert levels, work shifts, etc. Partner systems 18 includes patient information 21 which is provided to translator 22 via communication channel 17. With the patient information 21, the exemplary software-based system 20 can provide specific patient-related medical and personal information for dissemination to the recipients of an alarm event. In addition to the nurse call system 16 being the recipient of an alarm event, additional recipients are seen in the right hand portion of FIG. 2. For example, alarm or status information can be forwarded via communication channel 31 to anyone of a telephone interface 32 for communicating with phone system 34 via communication channel 31, a page interface 36 for communication with a pager system 38 via commutation channel 31, an electronic grease board/room/status client 40, a nurse call activity and performance reporting client 42, a call display client 44, etc.

In addition to reporting call requests via communication channel 15 to the nurse call system 16, a call and clear events channel 11 is provided between the nurse call system 16 and the exemplary software-based system 20. In the call and clear events operation, after a staff or alarm response has been attended to and completed, a responding person may initiate a clearing of the alarm event triggered by the patient monitoring system 12. The clearing may be initiated from the nurse call system 16 and processed by the exemplary software-based system 20.

It should be noted that an alarm event or status request is not necessarily limited to the nurse call system 16. Accordingly, additional systems such as the phone system 34, pager system 38, electronic greaseboard/room/status system 40, nurse call activity and performance reporting system 42, and call display system 44 may also be reported to, according to design preference. For example, statistical information on the response time to alarm events may be garnered from the exemplary software-based system 20 for performance evaluation, if so desired. Also, a more sophisticated visual display (44) may be alerted or interfaced with according to design preference. For example, a cardiologist may access from his computer, information regarding his patient, including the logs, statistics, current reading, etc. of patient monitoring system 12 attached to his patient. As an another example, a nurse administrator or staff nurse from her PC can query the exemplary software-based system 20 to obtain a historical record of an assigned patient. Similarly, a physician or medical professional can inquire of the statistics, data, information, etc. of any accessible component of the system via pager system 38 or a phone system 34. "War room" capabilities as enabled by the use of the electronic greaseboard/room/status system 40 can provide an overall or independent assessment of the system 30, and components in the system 30, specifically patients being monitored by the patient monitoring system 12.

Due to the bidirectional channel 31, each of the systems external to the exemplary software system 20 can be configured to receive information/alarm events or query and/or input information into the system status tables 27 of the exemplary software-based system 20 for querying the patient monitoring system 12.

In a preferred embodiment of the exemplary system 30, the advantages of integrating to a nurse call system 16 are evident when the system 16 publishes the patient monitor call set and call clear events to the exemplary software-based system 20. The same translator 22 and processing module 24 process feed display clients 44, including the electronic grease boards 31, call displays, room status displays, and nursing unit activity and response time reports, with patient-specific and/or patient monitor system-specific data. Using routing information from the staff to bed assignment clients, an alarm can be routed to the staff specifically responsible for the patient at the time, including standard multi-level rollover pages (escalating a call to another pager if the call has remained unanswered for a specified time).

In a preferred embodiment, for example, a TAP channel 13 is utilized, which is a RSS232 protocol. The potential for lost messages, particularly with an RS232 protocol such as TAP should be accounted for which is accomplished via checksum and handshake capability to prevent erroneous messages and allow retries for any message not received correctly. Synchronization between the nurse call system 16 and the patient monitoring system 12, typically a major role of the translators 22, is minimal within a preferred embodiment of the exemplary system since once an alarm is received by the nurse call system 16, it is fully integrated with the nurse call system 16 itself rather than the patient monitoring system 12 being solely responsible for maintaining and clearing the call.

In the preferred embodiment, for example, the link between systems is supervised with a sanity check, which the translator 22 would recognize as meaningless from a messaging standpoint, but would provide assurance that the link between systems was still live. That is, sanity check could be a heart beat, for example. If a heartbeat check is not a standard feature of the patient monitoring system 12, any page that can be automatically generated (such as an automatic patient monitor call every one to 5 minutes), can serve as the sanity heartbeat.

Thus, one of ordinary skill having read the disclosure herein may contemplate numerous other variations made feasible by the exemplary systems herein, without departing from the spirit and scope of this invention. For example, a simplified exemplary system may be used in a residential environment to enable monitoring of home-bound patients via the use of a public network system, for example, the Internet. The exemplary systems 10 and 30 described herein may also be configured as a single "machine." That is, exemplary systems 10 and 30 may be implemented on a single platform such as PC or microcontroller having an integrated patient monitoring system 12 or nurse call system 16 or partner system 18. The exemplary embodiments herein may accordingly be manufactured as stand alone units either in non-scalable or with scalable compatibility.

It should be appreciated that any of the communication system or channels illustrated in FIG. 1 and 2 may be of a standardized, proprietary, private, or public communication channel. Thus, acquisition, control, querying, alarm, updating, programming, etc. operations may be preformed remotely according to design preference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A patient monitoring and nurse call integration system, comprising:
    an event channel configured to identify a connection to patient equipment and a type of the patient equipment;
    a patient monitor translator in communication with the event channel;
    a nurse call translator in communication with the event channel;
    an assignment monitor configured to monitor staff and equipment assignments of a patient and patient equipment verification and location; and
    a processor in communication with the patient monitor translator and nurse call translator, wherein the processor executes instructions that determine monitoring information based on the information received from the event channel and interpret translated patient monitor communication and coordinate a communication via the nurse call translator to a nurse call system.

2. The system according to claim 1, further comprising:
    a system table containing information corresponding to an operational mode of a patient monitor, the system table being accessible by the processor.

3. The system according to claim 2, wherein the system table contains information corresponding to an operational mode of the nurse call system.

4. The system according to claim 2, wherein the system table contains a status of the patient monitor and the nurse call system.

5. The system according to claim 1, wherein the processor alters the communication of the nurse call translator based on a type of the patient monitor.

6. The system according to claim 1, wherein the processor alters the communication of the nurse call translator based on the interpreted translated patient monitor communication.

7. The system according to claim 1, further comprising:
    a partner staff and equipment location system; and a partner translator in communication with the processor.

8. The system according to claim 1, wherein the patient monitor translator translates communication received from a TAP channel.

9. The system according to claim 7, further comprising: a partner patient information system in communication with the partner translator.

10. The system according to claim 1, further comprising: a staff assignment controller that records assignments of staff.

11. The system according to claim 1, further comprising: a telephone system in communication with the processor.

12. The system according to claim 1, further comprising: a pager system in communication with the processor.

13. The system according to claim 1, further comprising: an electronic greaseboard in communication with the processor.

14. The system according to claim 1, further comprising: a secondary processor in communication with the processor.

15. The system according to claim 1, further comprising: a display in communication with the processor.

16. A method for patient monitoring and nurse call integration, comprising:
    identifying a connection to a patient monitoring system;
    identifying a type of the patient monitoring system;
    translating communication received from the patient monitoring system;
    verifying the patient monitoring system;
    determining a location of the patient monitoring system;
    monitoring staff and assignments and the patient monitoring system based on information determined from the identifying a connection to a patient monitoring system and the identifying a type of the patient monitoring system;
    processing the translated communication to assess at least one of an alarm and event communication;
    updating a status table to reflect a current state of equipment-to-staff assignment;

translating the processed communication into a nurse call system format; and communicating the translated processed communication to a nurse call system.

17. The method according to claim 16, further comprising:

translating at least one of a staff and an equipment location communication.

18. The method according to claim 16, further comprising:

assigning at least one of a staff and an equipment location information to the status table.

19. The method according to claim 16, further comprising:

alerting an assigned staff based on a processed translated communication.

20. The method according to claim 16, wherein the translating communication received from the patient monitoring system includes translating from a TAP standard.

21. The method according to claim 16, further comprising:

designating the patient monitor system type upon an initial translated communication received from the patient monitor system.

22. The method according to claim 16, further comprising:

resetting an alarm event from the nurse call system.

23. The method according to claim 16, further comprising: resetting an alarm event from a partner staff and equipment location system.

24. The method according to claim 21, further comprising:

alerting a designated person via telephone.

25. The method according to claim 24, wherein the designated person is alerted by pager.

26. The method according to claim 16, further comprising:

assigning patient information to the status table.

27. The method according to claim 16, further comprising:

assigning a staff member to a patient having a patient monitoring system.

28. The method according to claim 16, further comprising:

obtaining information from the status table from a non-patient-designated person.

29. A patient monitoring and nurse call integration system, comprising:

means for identifying a connection to patient equipment;

means for identifying a type of the patient equipment;

means for translating patient monitor communications;

means for translating nurse call communications;

means for verifying the patient equipment;

means for determining a location of the patient equipment;

means for monitoring staff and equipment assignments based on information received from the means for identifying a connection to patient equipment and the means for identifying a type of the patient equipment; and means for processing the translated patient monitor communications and executing instructions to coordinate communication to a nurse call system via the means for translating nurse call communications.

30. The system according to claim 29, further comprising:

means for updating a data table with information corresponding to an operational mode of a patient monitor.

31. The system according to claim 30, further comprising:

means for communicating to an external device for at least one of assessing a status or assignment of personnel or equipment for a patient.

* * * * *